United States Patent [19]

Felix et al.

[11] Patent Number: 5,563,044
[45] Date of Patent: Oct. 8, 1996

[54] PROCESS FOR THE ENZYMATIC PREPARATION OF GRF(1-44)NH$_2$

[75] Inventors: Arthur M. Felix, West Caldwell; Edgar P. Heimer, Nutley, both of N.J.

[73] Assignee: Hoffmann-La Roche Inc., Nutley, N.J.

[21] Appl. No.: 462,453

[22] Filed: Jun. 5, 1995

Related U.S. Application Data

[63] Continuation of Ser. No. 255,305, Jun. 7, 1994, abandoned, which is a continuation of Ser. No. 149,165, Nov. 8, 1993, abandoned, which is a continuation of Ser. No. 55,408, Apr. 29, 1993, abandoned, which is a continuation of Ser. No. 624,445, Dec. 10, 1990, abandoned.

[51] Int. Cl.$^6$ .............................. C12P 21/06; A61K 37/00
[52] U.S. Cl. ......................... 435/68.1; 435/69.4; 514/12; 530/324; 930/120
[58] Field of Search .................... 435/68.1, 69.4; 530/324; 514/12; 930/120

[56] References Cited

U.S. PATENT DOCUMENTS

| | | | |
|---|---|---|---|
| 4,517,181 | 5/1985 | Ling et al. | 514/12 |
| 4,518,586 | 5/1985 | Rivier et al. | 514/12 |
| 4,528,190 | 7/1985 | Vale, Jr. et al. | 514/12 |
| 4,529,595 | 7/1985 | Rivier et al. | 514/12 |
| 4,562,175 | 12/1985 | Chang et al. | 514/12 |
| 4,563,352 | 1/1986 | Rivier et al. | 514/12 |
| 4,585,756 | 4/1986 | Brazeau, Jr. et al. | 514/12 |
| 4,595,676 | 6/1986 | Spiess et al. | 514/12 |
| 4,605,643 | 8/1986 | Bohlen et al. | 514/12 |
| 4,610,976 | 9/1986 | Bohlen et al. | 514/12 |
| 4,617,149 | 10/1986 | Di Marchi et al. | 530/324 |
| 4,618,598 | 10/1986 | Conn | 514/6 |
| 4,622,312 | 11/1986 | Felix et al. | 514/12 |
| 4,626,523 | 12/1986 | Vale, Jr. et al. | 514/12 |
| 4,628,043 | 12/1986 | Spiess et al. | 514/12 |
| 4,649,039 | 3/1987 | Garlick et al. | 530/302 |
| 4,649,131 | 3/1987 | Felix et al. | 514/12 |
| 4,689,318 | 8/1987 | Kaiser et al. | 514/12 |
| 4,703,035 | 10/1987 | Rivier et al. | 514/12 |
| 4,704,450 | 11/1987 | Diaz et al. | 530/324 |
| 4,728,726 | 3/1988 | Rivier et al. | 530/324 |
| 4,732,972 | 3/1988 | Felix et al. | 530/324 |
| 4,734,399 | 3/1988 | Felix et al. | 514/12 |
| 4,783,524 | 11/1988 | Larsen et al. | 530/350 |
| 4,784,987 | 11/1988 | Rivier et al. | 514/12 |
| 4,914,189 | 4/1990 | Schally et al. | 530/324 |

FOREIGN PATENT DOCUMENTS

| | | |
|---|---|---|
| 23075 | 1/1984 | Australia. |
| 105759 | 10/1983 | European Pat. Off.. |
| 117034 | 1/1984 | European Pat. Off.. |
| 122818 | 2/1984 | European Pat. Off.. |
| 121764 | 3/1984 | European Pat. Off.. |
| 133282 | 7/1984 | European Pat. Off.. |
| 138416 | 9/1984 | European Pat. Off.. |
| 177819 | 9/1985 | European Pat. Off.. |
| 216517 | 8/1986 | European Pat. Off.. |
| 292334 | 5/1988 | European Pat. Off.. |
| 08776 | 8/1990 | European Pat. Off.. |
| 9007005 | 6/1990 | WIPO. |

OTHER PUBLICATIONS

Derwent Abstract No. 85–038853/07.
Science, 218(5), 585 (1982).
Nature, 300, 276 (1982).
Proc. Natl. Acad. Sci. USA 79, 7909 (1982).
J. Clin. Endo. Metab. 57(3), 677 (1983).
Unlisted Drugs, 35(3), 41 (1983).
Nature, 303, 532 (1983).
Biochem. Biophys. Res. Comm., 119(1), 265, (1984).
Medical World, Mar. 12, 1984, p. 37.
Proc. 7th Inter. Cong. Endo, Quebec City, Jul. 1–7, 1984, paper N–873.
Proc. 7th Inter. Cong. Endo, Quebec City, Jul. 1–7, 1984, Abstracts N–885, N–887/889, N–891/893, N–849.
Biochem. Biophys. Res. Comm. 123(2), 497 (1984).
Biochem. Biophys. Res. Comm. 123(2), 854 (1984).
New York Times. Apr. 17, 1988, p. Cl.
Molecular Endocrinology, 3(10), 1529 (1989).
Principals of Biochemistry, 5th Ed., pp. 1126–1129.
Life Sciences, 46(16), 999 (1990).
Biochemistry, 2(2), 252 (1963) Schoellmann et al.
J. Biochem. 88, 669, (1980) Tsuzuki et al.
Biochemia et Biophysicia Acta 830, 164 (1985) Riechmann et al.
J. Chem. Soc., Perkin Trans., 1, 1915 (1987) Le–Nguyen et al.
Int. J. Peptide Protein Res., 31, 86 (1988) Fournier et al.
J. Markussen, "Human Insulin by Transpeptidation of Porcine Insulin and Biosynthetic Precursors," MTP Press, Ltd., Boston (1987) (Book, not enclosed).
Russel et al. (1989) *Biochem. Soc. Trans.*, 7(6), 1145.
Klibanov (Jun. 1986) *Chemtech*, 354–359.
Kasche (1989) "The Proteolytic Enzymes", Beynow et al. eds., TRL Press, New York, pp. 125–143.
Jakulke et al. (1985) *Angew. Chem. Int. Ed. Engl.*, 24(2), 85–93.

*Primary Examiner*—John W. Rollins
*Assistant Examiner*—Jon P. Weber
*Attorney, Agent, or Firm*—George W. Johnston; Alan P. Kass

[57] ABSTRACT

GRF(1-44)-NH$_2$ is prepared by the trypsin catalyzed enzymatic coupling of Leu-NH$_2$ to GRF(1-43)-OH. The latter compound may be obtained by recombinant DNA synthesis. Thus the present method provides an economical pathway to the clinically important GRF(1-44)-NH$_2$ compound.

6 Claims, No Drawings

PROCESS FOR THE ENZYMATIC PREPARATION OF GRF(1-44)NH₂

This is a continuation of application Ser. No. 08/255,305, filed Jun. 7, 1994, now abandoned, which is a continuation of Ser. No. 08/149,165, filed Nov. 8, 1993, now abandoned, which is a continuation of Ser. No. 08/055,408, filed Apr. 29, 1993, now abandoned, which is a continuation of Ser. No. 07/624,445, filed Dec. 10, 1990, now abandoned.

BACKGROUND

Growth in animals is believed to be regulated by a cascade of bio-regulatory molecules. The hypothalamus produces a substance called Growth Hormone Releasing Factor (GRF) which in turn acts upon the pituitary to cause release of growth hormone (GH). GH stimulates the secretion of insulin growth factor (IGF) from the liver and other peripheral organs which binds to various cellular receptors stimulating the events required for linear growth. The pituitary is maintained under negative feedback control by somatostatin and IGF. GRF has been found to be enormously active and capable of stimulating the release of microgram per ml. levels of growth hormone in the blood. GRF can be utilized therapeutically in most of the areas now considered candidates for treatment by growth hormone, for example treatment of pituitary dwarfism, diabetes resulting from growth hormone production, enhancement of wound healing, treatment of burns or retardation of aging process.

The successful isolation of GRF was due partly to the discovery that pancreatic tumors associated with acromegaly ectopically produced large quantities of GRF. Three forms of GRF, consisting of peptides homologous from the amino-terminus of 44, 40 and 37 amino acids, were isolated by Guillemin et al [Science 218, 585–587 (1982)] and Rivier et al [Nature, 300, 276–278 (1982)]. The 44 amino acid amidated form of GRF, is considered to be the parent molecule and exhibits the full intrinsic activity and highest potency of the aforesaid forms of this molecule. The amidated carboxy-terminus is a key structural requirement for this high level of activity as the corresponding free acid (GRF(1-40)-OH) has a substantially lower level of activity. This is an important factor in developing low cost processes to produce these clinically important molecules.

Thus, since amidation of recombinant DNA produced peptides have not previously been possible by methods which could be conveniently employed in high yield steps, the preparation of the desired product, GRF(1-44)-NH₂, could previously be made only by use of conventional solid phase or solution phase peptide synthesis methods. The preparation of such a large peptide by these methods still represents a formidable technical challenge and the cost of production remains relatively high.

It is well recognized in the art that peptides can be produced in large scale and at lowest cost by employing recombinant DNA technology. Thus, it would be an important development in the commercialization of GRF(1-44)-NH₂ to be able to use a recombinantly produced peptide as substrate for the introduction of the amide functionality.

SUMMARY OF THE INVENTION

The instant invention is based on the discovery that GRF(1-44)-NH₂ can be conveniently prepared in good yield using GRF(1-43)-OH as the starting material. The latter compound can be produced by known recombinant DNA methods available to the art. Conversion of GRF(1-43)-OH to the desired product, GRF(1-44)-NH₂, is readily accompanied by the trypsin catalyzed coupling of H-Leu-NH₂ to GRF(1-43)-OH in accordance with the process of the present invention. Trypsin is well known in the art to catalyze the transpeptidation of peptides which contain carboxy-terminus arginine or lysine [J. Markussen, "Human Insulin by Transpeptidation of Porcine Insulin and Biosynthetic Precursors", MTP Press, Ltd., Boston (1987); H. Tsuzuti et al, J. Biochem., 88, 669–675 (1980); and L. Riechmann and V. Kasche, Biochemica et Biophysica Acta, 830, 164 (1985)]. The product, GRF-(1-44)-NH₂, can be readily isolated from the reaction media after quenching with acetic acid by use of peptide purification methods known in the art, most preferably by HPLC followed by desalting in a manner known per se.

DETAILED DESCRIPTION

The process of the present invention can be conveniently carried out by preparing a reaction mixture containing a solution of trypsin and Leu-NH₂ to which is added GRF(1-43)-OH, preferably obtained by recombinant DNA synthesis. The solvent employed for the present invention can be any solvent utilized in trypsin catalysis and is compatible with peptide synthesis. A preferred solvent for the purposes of the invention is dimethylacetamide (DMAC).

Preferably, the Leu-NH₂ solution is prepared by dissolving a Leu-NH₂ mineral acid salt (e.g. HCl) in water, adding dilute base (e.g. NaOH) to pH 8.0, lyophilizing and taking up the residue in the desired reaction solvent e.g. DMAC.

Similarly, the trypsin solution can be conveniently prepared by dissolving trypsin in dilute aqueous $CaCl_2$ (0.1M). The trypsin and Leu-NH₂ solutions are mixed (25:75 v/v) and the reaction started by addition of GRF(1-43)-OH. The reaction can be conveniently carried out at room temperature. Conversion of the starting compound to the desired end product can be conveniently followed by removing aliquots from the reaction mixture, diluting with acetic acid to quench the reaction, and then applying the solution to an HPLC column. Usually the reaction is complete in about 3.5 hours.

The reaction mixture is quenched by the addition of glacial acetic acid and diluting with water. Fractionation on HPLC (e.g. Lichrosorb RP-8 column) followed by desalting (e.g. Waters μBondapak C-18 column) and lyophilization provides the purified product, GRF (1-44)-NH₂, in good yield.

The present invention will be illustrated in a preferred embodiment in the following example which is set forth for the purpose of illustration only.

MATERIALS AND METHODS

All amino acid derivatives were of the L-configuration and purchased from Bachem (Torrance, Calif.). Porcine trypsin (Sigma, Type IX) was assayed against $N^\alpha$ benzoyl-L-arginine ethyl ester (BAEE) and the specific activity determined to be $1.85 \times 10^4$ U/mg. It was treated with N-tosyl-L-phenylalaninechloromethylketone (TPCK) [G. Schoellman and E. Shaw, Biochemistry, 2, 252 (1983)] and dialyzed extensively against distilled water and lyophilized to give $2.02 \times 10^4$ U/mg. N,N-Dimethylacetamide (Kodak, Spectro Grade) and 1,4-butanediol (Sigma, Gold Label) were dried over 3A sieves. Tryptic digests were carried out in solutions of the peptide (1 mg/mL) and bovine trypsin (Millipore, 0.1 mg/mL) in 0.5M $NH_4HCO_3$ (pH 8.0) for 20 hours. All pH measurements were made with a glass electrode. In vitro bioassays were done in rat pituitary cell cultures and using a specific rat growth hormone radioimmunoassay as previously described (P. Brazeau et al., Proc. Natl. Acad. Sci. USA, 79, 7909 (1982). GRF(1-43)-OH was prepared by solid-phase synthesis as follows:

Boc-Leu-phenylacetamidomethyl (PAM)-resin (4.0 g, 0.33 mmol/g, 1.32 mmol) was introduced into two 50 mL reaction vessels and solid phase peptide synthesis was carried out by the BOP procedure [A. Fournier, C.-T. Wang, and A. M. Felix, Int. J. Peptide Protein Res., 31, 86–97, (1988)]. The couplings were performed using the in situ neutralization coupling protocol [D. Le-Nguyen, A. Hertz, and B. Castro, J. Chem. Soc. Perkin Trans. 1, 1915–1919, (1987)] for a total of 42 cycles to give 5.3 g of protected GRF(1- 43)-PAM resin. A 1 g portion of the peptide-resin was treated with anhydrous HF (containing ca. 23% n-propanethiol) for 2 hr. at 0° C., evaporated at 0° C. (high vac; CaO trap), triturated with EtOAc and extracted with TFA and filtered. The filtrate was evaporated and the residue dried to give 421 mg of crude GRF(1-43)-OH. The crude peptide was dissolved in 25 mL of 0.5% TFA/$H_2O$, filtered (0.45μ Type HA Millipore filter) and loaded onto a Dupont Pro-10 C-8 column (2.2×25 cm). The column was eluted with (A) $H_2O$ (0.5% TFA)—(B) $CH_3CN$ (0.25% TFA) in a linear gradient from 20% (B) to 45% (B) in 60 min with a flow rate of 21 mL/min. Fractions were collected (1 min/fraction) and aliquots analyzed by the analytical HPLC system: Column: Lichrosorb RP-8 (5 m); (A) 0.1M $HClO_4$ (pH 2.5)—(B) $CH_3CN$; 40% (B) to 60% (B) in 20 min at 1 mL/min; 0.2 AUFS; 206 nm. The product emerged in fraction 70 which was evaporated and lyophilized to give 17 mg of material. The product was shown to be homogenous by analytical HPLC and gave the expected amino acid composition after acid hydrolysis (Amino Acid Anal: 6N HCl; 110° C.; 24 h): Asp, 4.09 (4); Thr, 0.91 (1); Ser, 3.96 (4); Glu, 7.78 (7); Gly, 3.11 (3); Ala, 4.82 (5); Val, 0.95 (1); Met 1.03 (1); Ile, 1.76 (2); Leu, 4.29 (4); Tyr, 1.80 (2); Phe, 0.82 (1); Lys, 2.15 (2); Arg, 6.06 (6). Confirmation of structure was provided by FAB mass spectrometry. Calcd.: $(M+H)^+$, 4928.5 Found, 4928.5.

EXAMPLE 1

A. 1.25M solution of Leu-$NH_2$ in DMAC was prepared by dissolving Leu-$NH_2$.HCl (1.33 g, 7.98 mmol) in 5.0 mL of water, titrating to pH 8.0 with 1M NaOH, lyophilizing, and taking up the residue in 6.4 ml of DMAC. The NaCl precipitate was removed by filtering through a fine glass frit to give a clear solution of pH 9.25.

A solution of trypsin (14.5 μM) and Leu-$NH_2$ (0.95M) in 76:24 (v:v) DMAC/$H_2O$ (pH 8.3) was prepared by dissolving trypsin (0.205 mg, 8.72 mmol) in 0.1M $CaCl_2$ (300 μL) followed by addition of the above 1.25M Leu-$NH_2$ in DMAC (950 μL). GRF(1-43)-OH (5.15 mg, 0.864 μmol) was dissolved in 0.600 mL of the above enzyme preparation and kept at room temperature (ca. 22° C.). The progress of the reaction was monitored by removing 1 μL aliquots (16 μL total), diluting in 200 μL portions of 20% acetic acid, and applying to the HPLC column.

The reaction was halted at the 3.5 hr mark by adding glacial acetic acid (0.20 mL) and diluting to 2.4 mL with water. The yield at this point was 60% as determined by analytical HPLC. A small portion (5 mL) of the reaction mixture was set aside for further monitoring before quenching with acetic acid. The reaction mixture was purified as follows:

Analytical and preparative HPLC were carried out on a Lichrosorb RP-8 (5μ) column (0.4×25 cm). Eluants: (A) 0.1M $NaClO_4$ (pH 2.5)—(B) $CH_3CN$. The flow rate was 1.5 mL/min and gradients of 38–41% (B) in 10 min and 31–35% (B) in 90 min were employed for the analytical and preparative runs, respectively. Fractions from the Lichrosorb RP-8 column were desalted on a Waters μBondapak (C-18 column (0.4×30 cm). Eluants: (A) $H_2O$ (0.025% TFA)—(B) $CH_3CN$ (0.025% TFA) and a flow rate of 2.0 mL/min was used. The sample was loaded and the column washed with 15% (B) for 20 min and the column eluted using a gradient of 15–40% (B) in 20 min. and the product-containing fractions were pooled and lyophilized.

The final yield of GRF(1-44)-$NH_2$ was 1.95 mg (0.322 μmol, 37%). FAB-MS: $(M+H)^+$ Calc: 5040.7, Found: 5040.5. Amino Acid Anal (6M HCl; 110° C., 72 h.): Asp, 4.12(4); Thr, 0.97(1); Ser, 3.65(4); Glu, 7.54(7); Gly, 2.99(3); Ala, 5.27(5); Val, 1.04(1); Met, 0.92(1); Ile, 2.01(2); Leu, 5.13(5); Tyr, 1.87(2); Phe, 0.91(1); Lys, 2.03(2); Arg, 5.54(6). In vitro biological potency: 0.92±0.22. [rat pituitary in vitro bioassay in which the potency of GRF (1-44)-$NH_2$ is 1.00]. Tryptic mapping, by analytical HPLC, was identical to that of a chemically synthesized standard of GRF(1-44)-$NH_2$.

We claim:

1. A process for the preparation of GRF(1-44)-$NH_2$ which process comprises reacting GRF(1-43)-OH with Leu-$NH_2$ in the presence of catalytic amounts of trypsin at a pH of about 8.0 in dimethylacetamide and isolating GRF(1-44)-$NH_2$ from the reaction mixture.

2. The process of claim 1 wherein said GRF(1-43)-OH is produced by recombinant DNA synthesis.

3. The process of claim 1 wherein the reaction is carried out at room temperature.

4. The process of claim 1 wherein the reaction mixture is quenched after completion of the reaction by mixing with acetic acid.

5. The process of claim 1 wherein said GRF(1-44)-$NH_2$ is isolated by use of HPLC.

6. The process of claim 5 wherein said GRF(1-44)-$NH_2$ is desalted and lyophilized after HPLC isolation.

* * * * *